US006759571B1

(12) United States Patent
Robertson (10) Patent No.: US 6,759,571 B1
(45) Date of Patent: Jul. 6, 2004

(54) METHOD OF SUPPRESSING GENE EXPRESSION IN PLANTS

(75) Inventor: Dominique Robertson, Cary, NC (US)

(73) Assignee: North Carolina State University, Raleigh, NC (US)

(*) Notice: Subject to any disclaimer, the term of this patent is extended or adjusted under 35 U.S.C. 154(b) by 0 days.

(21) Appl. No.: 09/281,528

(22) Filed: Mar. 30, 1999

Related U.S. Application Data
(60) Provisional application No. 60/080,383, filed on Apr. 1, 1998.

(51) Int. Cl.[7] .......................... C12N 15/09; C12N 15/11; C12N 15/69; C12N 15/82; A01H 5/00
(52) U.S. Cl. ..................... 800/285; 435/320.1; 435/419; 435/468
(58) Field of Search ................................ 800/285, 286, 800/280, 298; 435/320.1, 419, 468; 536/237.2

(56) References Cited

U.S. PATENT DOCUMENTS

| | | | |
|---|---|---|---|
| 5,231,020 A | 7/1993 | Jorgensen et al. | 435/468 |
| 5,316,931 A | 5/1994 | Donson et al. | 435/468 |
| 5,589,367 A | 12/1996 | Donson et al. | 435/468 |
| 5,589,379 A | * 12/1996 | Kridl et al. | 435/240.4 |
| 5,650,303 A | 7/1997 | Kridl et al. | 435/91.41 |
| 5,922,602 A | 7/1999 | Kumagai et al. | 435/468 |
| 5,981,236 A | 11/1999 | Kridl et al. | 435/91.41 |
| 6,077,992 A | 6/2000 | Yadav | 800/278 |

FOREIGN PATENT DOCUMENTS

| | | | |
|---|---|---|---|
| EP | 0 221 044 A1 | 5/1987 | ........... C12N/15/00 |
| EP | 1 013 771 A1 | 6/2000 | ........... C12N/15/86 |
| WO | WO 95/34668 | 12/1995 | ........... C12N/15/83 |
| WO | WO 99/22003 | 5/1999 | |

OTHER PUBLICATIONS

Koes et al. , Plant Cell, vol. 2, 1990, pp. 379–392.*
Voinnet , O., Trends in Genetics, 2001, vol. 17, pp. 449–459.*
Metzlaff et al., Cell, 1997, vol. 88, pp. 845–854.*
Theologis et al., Plant Physiol., 1992, vol. 100, pp. 549–551.*
Meyer et al., Gene, 1992, vol. 110, pp. 213–217.*
Voinnet et al., Suppression of gene silencing: A general strategy used by diverse DNA and RNA viruses of plants, 1999, PNAS, vol. 96, pp. 14147–14152.*
Covey SN et al( 2000) Plant DNA viruses and gene silencing. Plant Molecular Biology 43: 307–322.*
Neuhuber et al. (1994) Susceptibility of transgene loci to homology–dependent gene silencing Mol Gen Genet 244:230–241.*
Atkinson et al (1998) Post Transcriptional silencing of chalcone snthase in petunia using a geminvirus based episomal vector. The Plant Journal 15 (5) 593–604.*
Kjemtrup et al (1998)Gene Silencing from plant carried by a Geminivirus, The Plant Journal 14(1):91–100).*
Matzeit, V et al (1991) The Plant Cell 3: 247–258).*
Fromm, ME et al (1986) Nature 319:791–93.*
Paszkowski J et al (1992) Plant Molecular Biology 19:825–836.*
Hayes et al (1988) Nature 334: 179–182.*
Stanley et al (1985) J Gen Virol Pseudorecombinants between cloned DNAs of two isolates of cassava latent virus 66: 1055–1061.
Angell S.M. et al.; *Consistent gene silencing in transgenic plants expressing a replicating potato virus X RNA*; The EMBO Journal; 16:3675–3684 (1997).
Brough C.L. et al.; *Effects of Mutagenesis in vitro on the Ability of Cloned Tomato Golden Mosaic Virus DNA to Infect Nicotiana benthamiana Plants*, J. Gen. Virol; 69:503–514 (1988).
Davenport G. et al.; *Mutation of the GKS motif of the RNA–dependent RNA polymerase from potato virus X disables or eliminates virus replication*; Journal of General Virology; 78:1247–1251 (1997).
Dawson W.O.; *Gene silencing and virus resistance: a common mechanism*; Trends in Plant Science; 1(4):107–108 (1996).
English J.E. et al.; *Suppression of Virus Accumulation in Transgenic Plants Exhibiting Silencing of Nuclear Genes*; The Plant Cell; 8:179–188 (1996).
Goodwin J. et al.; *Genetic and Biochemical Dissection of Transgenic RNA–Mediated Virus Resistance*; The Plant Cell; 8:95–105 (1996).
Jeffrey J.L. et al.; *Genetic Requirements for Local and Systemic Movement of Tomato Golden Mosaic Virus in Infected Plants*; Virology; 223:208–218 (1996).
Kanevski I.F. et al.; *Tobacco lines with high copy number of replicating recombinant geminivirus vectors after biolistic DNA delivery*; The Plant Journal; 2(4):457–463 (1992).
Kumagai M.H. et al.; *Cytoplsmic inhibition of carotenoid biosynthesis with virus–derived RNA*; Proc. Natl. Acad. Sci. USA; 92:1679–1683 (1995).
Kumpatla S.P. et al.; *Epigenetic Transcriptional Silencing and 5–Azacytidine–Mediated Reactivation of a Complex Transgene in Rice*; Plant Physiol.; 115:361–373 (1997).
Meyer P.; *Repeat–Induced Gene Silencing: Common Mechanisms in Plants and Fungi*; Biol. Chem. Hoppe Savier; 377:87–95 (1996).

(List continued on next page.)

Primary Examiner—Ashwin Mehta
(74) Attorney, Agent, or Firm—Myers Bigel Sibley & Sajovec, P.A.

(57) ABSTRACT

The introduction of DNA episomes into plant cells to reduce or prevent the expression of endogenous nuclear or chromosomal genes is described. Geminivirus vectors to provide systemic silencing of an endogenous plant gene in a treated plant are described.

28 Claims, 3 Drawing Sheets

OTHER PUBLICATIONS

Mueller E. et al.; *Homology–dependent resistance: transgenic virus resistance in plants related to homology–dependent gene silencing; The Plant Journal*; 7(6):1001–1013 (1995).

Nagar S. et al.; *A Geminivirus Induces Expression of a Host DNA Synthesis Protein in Terminally Differentiated Plant Cells; The Plant Cell*; 7:705–719 (1995).

Neuhuber F. et al.; *Susceptibility of transgene loci to homology–dependent gene silencing; Mol. Gen. Genet.*; 244:230–241 (1994).

Palauqui J.C. et al.; *Systemic acquired silencing: transgene–specific post–transcriptional silencing is transmitted by grafting from silenced stocks to non–silenced scions The EMBO Journal*; 16(15):4738–4745 (1997).

Park Y.D. et al.; *Gene silencing mediated by promoter homology occurs at the level of transcription and results in meiotically heritable alternations in methylation and gene activity; The Plant Journal*; 9(2):183–194 (1996).

Ratcliff F. et al.; *A Similarity Between Viral Defense and Gene Silencing in Plants; Science*; 276:1558:1560 (1997).

Stam M. et al.; *Post–transcriptional silencing of chalcone synthase in Petunia by inverted transgene repeats; The Plant Journal*; 12(1):63–82 (1997).

Tanzer M. M. et al.; *Characterization of Post–Transcriptionally Suppressed Transgene Expression that Confers Resistance to Tobacco Etch Virus Infection in Tobacco The Plant Cell*; 9:1411–1423 (1997).

Timmermans M. et al.; *Geminiviruses and their uses as extrachromosomal replicons; Annu. Rev. Plan Physiol.*; 45:79–112 (1994).

Voinett O. et al.; *Systemic signalling in gene silencing; Nature*; 389(6651):553 (1997).

Ye F. et al.; *RIGS (repeat–induced gene silencing) in Arabidopsis is transcriptional and alters chromatin configuration; Proc. Natl. Acad. Science USA* 93:10881 (1996).

Atkinson et al.; *Post–Transcriptional Silencing of Chalcone Synthase in Petunia Using a Geminivirus–Based Episomal Vector, The Plant Journal*, vol. 15(5):593–604 (1998).

Baulcombe et al.; *Ectopic Pairing of Homologous DNA and Post–Transcriptional Gene Silencing in Transgenic Plants, Current Opinion in Biotechnology*, vol. 7(2):173–180 (1996).

Hanley–Bowdoin et al.; *Transient Expression of Heterologous RNAs Using Tomato Golden Mosaic Virus, Nucleic Acid Research*, vol. 16(22):10511–10528 (1988).

Hayes et al.; *Gene Amplification and Expression in Plants by a Replicating Geminvirus Vector, Nature*, vol. 334:179–182 (1988).

Kjemtrup et al.; *Gene Silencing from Plant DNA Carried by a Geminivirus, The Plant Journal*, vol. 14(1): 91–100 (1998).

PCT International Search Report of PCT/US 99/06082, dated Jul. 21, 1999.

Abouzid, A.M. et al., *Cloning, Identification, and Partial Sequencing of the Genomic Components of a Geminivirus Infecting the Brassicaceae, Phytopathology*, Abstract #A70, vol. 82: 1070 (1992).

Baulcombe D.C., *RNA as a Target and an Initiator of Post–Transcriptional Gene Silencing in Transgenic Plants, Plant Molecular Biology*, 32: 79–88 (1996).

Hill, J.E. et al, *Asymmetric Infectivity of Pseudorecombinants of Cabbage Leaf Curl Virus and Squash Leaf Curl Virus: Implications for Bipartite Geminivirus Evolution and Movement, Virology*, 250:283–292 (1998).

Jones C.G. et al., *Down Regulation of Two Non–homologous Endogenous Genes with a Single Chimeric Gene construct*, In: Mechanisms and Applications of Gene Silencing, Edited by D. Grierson, G.W. Lycett, and G.A. Tucker, Nottingham University Press, Nottingham, UK, pp 85–95 (1996).

Jones C.G., et al., *The Effect of Chimeric Trangene Architecture on Co–ordinated Gene Silencing, Planta*, 204: 499–505 (1998).

Seymour G.B. et al., *Down–regulation of Two Non–homologous Endogenous Tomato Genes with a Single Chimaeric Gene Construct, Plant Molecular Biology*, 23:1–9 (1993).

Strandberg, J.O. et al., *A New Geminivirus with a Broad Host Range in the Brassicaceae, Phytopathology*, Abstract #837, vol. 81:1244 (1991).

* cited by examiner

METHOD OF SUPPRESSING GENE EXPRESSION IN PLANTS

This application claims the benefit of U.S. Provisional Application No. 60/080,383, filed Apr. 1, 1998.

FIELD OF THE INVENTION

The present invention relates to the introduction of DNA episomes into plant cells to silence nuclear or chromosomal genes. More particularly, this invention relates to use of geminivirus vectors to provide systemic silencing of an endogenous plant gene in a treated plant.

BACKGROUND OF THE INVENTION

Gene silencing in plants typically refers to either the suppression of an endogenous gene by the introduction of a related transgene, or to the suppression of genes introduced at ectopic positions in plant genomes. Some examples of pathogen-derived host resistance to RNA viruses have been attributed to a gene silencing mechanism (Covey et al., *Nature* 386:781 (1997); Mueller et al. *Plant J.* 7:1001 (1995); Ratcliff et al., *Science* 276:1558 (1997); Tanzer et al., *Plant Cell* 9:1411 (1997). Transcriptional gene silencing has been hypothesized to involve DNA/DNA pairing, DNA methylation or heterochromatinization (Kumpatia et al., *Plant Physiol.* 115:361 (1997); Neuhuber, *Mol. Gen. Genetics* 247:264 (1995); Park et al., *Plant J.* 9:183 (1996)). Repeated DNA has a tendency to undergo transcriptional silencing, which may be associated with changes in chromatin structure (Meyer, *Biol. Chem. Hoppe Sayler* 377:87 (1996); Ye and Signer, *Proc. Natl. Acad. Sci. USA* 93:10881 (1996)), as well as to induce certain types of post-transcriptional silencing (Stam et al., *Plant J.* 12:63 (1997)). Both cytoplasmic and nuclear events have been implicated in gene silencing. Post-transcriptional gene silencing may require accumulation of a threshold level of mRNA, after which degradation of all homologous gene transcripts occurs, and may be potentiated by aberrant mRNAs. Metzlaff et al., *Cell* 88:845 (1997); Mueller et al., *Plant J.* 7:1001 (1995).

Figure 1A:
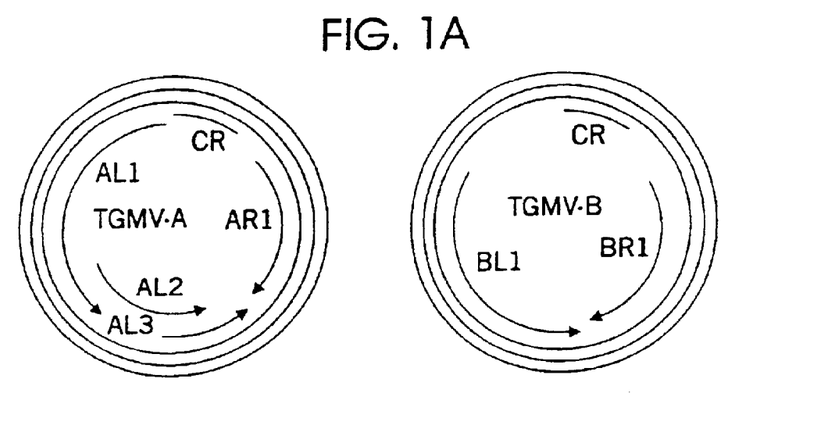
FIG. 1A shows the TGMV A and B genetic components; each contain a common region (CR) that includes the origin of replication. AL1, AL2 and AL3 are viral genes needed for replication and gene expression. The AR1 gene encodes the coat protein. The B component encodes two movement proteins, BL1 and BR1.

Geminiviruses are single-stranded DNA viruses that replicate through double-stranded DNA intermediates using the plant DNA replication machinery. Geminiviruses replicate in the nucleus, and foreign DNA can be stably integrated into the viral genome without significantly affecting replication or movement. Tomato golden mosaic virus (TGMV) is a bipartite geminivirus with a genome of two circular molecules, TGMV-A and TGMV-B (FIG. 1). TGMV-A replicates autonomously. The TGMV coat protein (AR1) is dispensable for replication and movement in *N. Benthamiana* and can be replaced with up to 800 bp of foreign DNA, which is stably maintained in the viral genome (Elmer and Rogers, *Nucl. Acids. Res.* 18:2001 (1990)).

A plant virus may systemically infect a plant by spreading from the initially infected cell to neighboring cells, and subsequently throughout the plant. Plant cell walls prevent the random cell-to-cell transfer of virus, but channels (plasmodesmata) in plant cell walls provide an intercellular continuum through which virus particles or viral nucleic acids may move. Viral movement via plasmodesmata is mediated by virus-encoded proteins. Citovsky et al., *BioEssays* 13:373 (1991). Additionally, movement of virus to parts of the plant distant from the point of initial infection can occur via companion cells and sieve elements of the phloem. However, even in systemically infected plants the distribution of the virus may not be uniform. Certain areas of the plant, even within a tissue or a structure, may contain lower or higher amounts of virus than neighboring areas.

SUMMARY OF THE INVENTION

A first aspect of the present invention is a geminivirus silencing vector comprising a geminivirus genome which contains heterologous DNA, where the heterologous DNA is identical to, or has substantial sequence similarity to, a gene endogenous to a plant or a fragment of a gene endogenous to a plant.

A further aspect of the present invention is a DNA construct comprising a geminivirus genome, where the DNA encoding the geminivirus coat protein has been replaced in part or in total with heterologous DNA identical to, or having substantial sequence similarity to, an endogenous plant gene or a fragment of an endogenous plant gene.

A further aspect of the present invention is a DNA construct comprising, in the 5' to 3' direction, a geminivirus origin of replication; DNA encoding proteins necessary for replication of the DNA construct; and a heterologous DNA segment identical to, or having substantial sequence similarity to, an endogenous plant gene or a fragment of an endogenous plant gene.

A further aspect of the present invention is a DNA construct comprising, in the 5' to 3' direction, a geminivirus origin of replication; DNA encoding proteins necessary for replication of the DNA construct; and a heterologous DNA segment identical to, or having substantial sequence similarity to, an endogenous plant gene or a fragment of an endogenous plant gene. This DNA construct is subject to the proviso that the DNA segment is not operably linked to a promoter.

A further aspect of the present invention is a method of silencing the expression of a plant gene in a plant cell, by inoculating the plant cell with a DNA construct or silencing vector as described above.

A further aspect of the present system is a method of systemically silencing expression of a plant gene in a plant, by inoculating the plant with an endogenous plant gene or a fragment of an endogenous plant gene.

A further aspect of the present invention is a method of screening isolated plant DNA for function. The method comprises preparing a DNA vector as describe above, containing a DNA segment identical to, or having substantial sequence similarity to, the isolated plant DNA or a fragment thereof. A test plant is then inoculated with the vector and allowed to grow for a period of time, then compared to a non-inoculated or sham inoculated control plant. Differences between the inoculated and control plants indicate the function of the isolated plant DNA.

BRIEF DESCRIPTION OF THE DRAWINGS

FIG. 4 shows the results of electrophoretic separation of uncut DNA probed with an 850 bp TGMV-A-specific DNA fragment. DNA was isolated from plants showing systemic symptoms or variegation; the tissue tested was either yellow (Y; yellow-white tissue); mixed (M; borders of green and yellow areas); or green (G; green tissue lacking visible traces of variegation or viral symptoms). Lane 1 shows wildtype TGMV DNA with three DNA forms: open circular (OC), closed circular (CC) and ssDNA. Lanes 2–4 show viral DNA isolated from N. benthamiana infected with TGMV::su5S; lanes 5–7 show viral DNA from plants inoculated with TGMV::su5F; lanes 8–10, viral DNA from plants inoculated with TGMV::su5 A. The bottom panel is the same blot as described above, but was probed with a 786 bp fragment from su. This gel indicates that TGMV::su DNA accumulation is lower in yellow tissue than in yellow-green borders.

DETAILED DESCRIPTION OF THE INVENTION

The geminivirus tomato golden mosaic virus (TGMV) replicates in plant cell nuclei and expresses genes from high copy number DNA episomes. TGMV was used as vector to determine whether episomal DNA could cause silencing of homologous chromosomal genes. Two markers were used to assess silencing: (1) the sulfur allele (su) of magnesium chelatase, an enzyme required for chlorophyll formation; and (2) the firefly luciferase gene (luc). Various portions of both marker genes were inserted into TGMV in place of the coat protein open-reading frame and the constructs were introduced into intact plants using particle bombardment. When TGMV vectors carrying fragments of su (TGMV::su) were introduced into leaves of wild-type Nicotiana benthamiana, circular, yellow spots with an area of several hundred cells formed after 3–5 days. Systemic movement of TGMV::su subsequently produced variegated leaf and stem tissue. Fragments that caused silencing included a 786 bp 5' fragment of the 1392 bp su cDNA in sense and antisense orientation, and a 403 bp 3' fragment of su cDNA. TGMV::su-induced silencing was propagated through tissue culture, along with the viral episome, but was not retained through meiosis. Systemic down-regulation of a constitutively expressed luciferase transgene in plants was achieved following infection with TGMV vectors carrying a 623 bp portion of luc in sense or anti-sense orientation.

The present results demonstrate that DNA carried on episomes can silence active, chromosomal gene expression, and that DNA plant virus genomes (and particularly geminivirus genomes) can provide a mechanism for the systemic suppression of gene expression in plants. The present inventors show that a nuclear-localized DNA virus (such as the TGMV geminivirus) carrying sequences complementary to (i.e., homologous to, or having substantial sequence similarity to) chromosomal genes can silence the chromosomal gene.

The present inventors determined that silencing of nuclear genes can be triggered by homologous sequences carried by a DNA episome, such as a geminivirus construct. Where the episome is capable of spreading from cell to cell in a plant (or capable of producing a diffusable silencing factor), systemic silencing of chromosomal genes can be achieved. A TGMV vector was used to test sense, anti-sense and frame-shifted versions of a 786 bp 5' fragment of the magnesium chelatase gene (su), as well as a non-overlapping 403 bp 3' sense fragment of su. In each case, similar variegated phenotypes were produced after infection. The lack of chloroplast transit sequences in the two su sense fragments used for silencing (the 5' sense fragment and the 3' fragment), as well as the anti-sense result, indicate that defective protein-protein interactions in the multisubunit magnesium chelatase complex are not responsible for the lack of chlorophyll formation. In addition, silencing of the luciferase transgene by TGMV::luc also appears to occur at the RNA or DNA level, as both sense and anti-sense versions of the luc fragment downregulate transgene expression. Luciferase was used to test downregulation by episomal sequences because its activity can be visualized non-destructively. The activity of luciferase is known to be directly proportional to the accumulation of a single gene product (Millar et al, *Plant Cell* 4:1075 (1992)). Both luciferase activity and mRNA accumulation were markedly decreased in TGMV::luc-infected plants (see FIG. 4).

Previous reports have demonstrated gene expression from geminivirus-derived episomes (reviewed in Timmermans et al., *Annu. Rev. Plant Physiol.* 45:79, 1994). A direct correlation between episome copy number and gene expression was shown in cultured cells for TGMV carrying the neo gene (Kanevski et al., *Plant J.* 2:457, 1992). The present experiments differ in that there was no selection for gene expression, there was homology (i.e., sequence identity or substantial sequence similarity) between the episomal and chromosomal sequences, and only partial copies of the silenced endogenous genes (su or luc genes) were carried in episomes. The silencing of chromosomal gene expression by episomal DNA is demonstrated; more specifically, the ability to silence endogenous gene expression systemically in a plant using a plant virus construct is demonstrated.

The present invention permits the modulation of gene expression in plants, without the need for transformation of plants cells with subsequent regeneration of whole plants. The present methods also allow the modification of plant gene expression without the modification of the germplasm.

Geminiviruses and Badnaviruses

The geminiviruses are single-stranded plant DNA viruses. They possess a circular single-stranded (ss) DNA as their genome encapsidated in twinned "geminate" icosahedral particles. The encapsidated ss DNAs are replicated through circular double stranded DNA intermediates in the nucleus of the host cell, presumably by a rolling circle mechanism. Viral DNA replication, which results in the simulation of both single and double stranded viral DNAs in large amounts, involves the expression of only a small number of viral proteins that are necessary either for the replication process itself or facilitates replication or viral transcription. The geminiviruses therefore appear to rely primarily on the machinery of the host to copy their genomes and express their genes.

Geminiviruses are subdivided on the basis of host range in either monocots or dicots and whether the insect vector is a leaf hopper or a white fly species. Monocot-infecting geminiviruses are typically transmitted by leaf hoppers and their genome comprises a single ss DNA component about 2.7 kb in size (monopartite geminivirus); this type of genome, the smallest known infectious DNA, is typified by wheat dwarf virus which is one of a number from the subgroup that have been cloned and sequenced. Most geminivirus that infect dicot hosts are transmitted by the white fly and possess a bipartite genome comprising similarly sized DNAs (usually termed A and B) as illustrated by African cassava mosaic virus (ACMV), tomato golden mosaic virus (TGMV) and potato yellow mosaic virus. For successful infection of plants, both genomic components are required. Beet curly top virus occupies a unique intermediary position between the above two subgroups as it infects dicots but contains only a single genomic component equivalent to DNA A, possibly as a result of adaption to leaf hopper transmission.

The bipartite subgroup contains only the viruses that infect dicots. Exemplary is the African Cassava Mosaic Virus (ACMV) and the Tomato Golden Mosaic Virus (TGMV). TGMV, like ACMV, is composed of two circular DNA molecules of the same size, both of which are required for infectivity. Sequence analysis of the two genome components reveals six open reading frames (ORFs); four of the ORFs are encoded by DNA A and two by DNA B. On both components, the ORFs diverge from a conserved 230 nucleotide intergenic region (common region) and are transcribed bidirectionally from double stranded replicative form DNA. The ORFs are named according to genome component and orientation relative to the common region (i.e., left versus right). The AL2 gene product transactivates expression of the TGMV coat protein gene, which is also sometimes known as "AR1". Functions have not yet been attributed to some of the ORFs in the geminivirus genomes. However, it is known that certain proteins are involved in the replication of viral DNA (REP genes). See, e.g., Elmer et al., *Nucleic Acids Res.* 16:7043 (1988); Hatta and Francki, *Virology* 92:428 (1979).

The A genome component contains all viral information necessary for the replication and encapsidation of viral DNA, while the B component encodes functions required for movement of the virus through the infected plant. The DNA A component of these viruses is capable of autonomous replication in plant cells in the absence of DNA B when inserted as a greater than full length copy into the genome of plant cells, or when a copy is electroporated into plant cells. In monopartite geminivirus genomes, the single genomic compenent contains all viral information necessary for replication, encapsidation, and movement of the virus.

Little is known about the interaction of geminiviruses with their hosts. Because they replicate to high copy numbers in plant nuclei, they may have evolved mechanisms to evade homology sensing and silencing mechanisms. The present inventors have determined that insertion of plant DNA into the geminivirus genome can trigger gene silencing in the host plant.

Badnaviruses are a genus of plant viruses having double-stranded DNA genomes. Specific badnavirus include cacao swollen shoot virus and rice tungro bacilliform virus (RTBV). Most badnavirus have a narrow host range and are transmitted by insect vectors. In the badnaviruses, a single Open Reading Frame (ORF) may encode the movement protein, coat protein, protease and reverse transcriptase; the final products are produced by proteolytic processing.

Episomally-mediated Gene Silencing

The present invention provides methods of silencing endogenous plant genes using DNA episomes, and provides constructs for the use in such methods. The episomal DNA carries a DNA sequence homologous to the endogenous plant gene to be silenced, or homologous to a fragment of the endogenous plant gene to be silenced. The DNA episomes must be able to replicate to multiple copy numbers in plant nuclei; where systemic silencing is desired, the episome should be able to move from cell-to-cell in the plant or to induce the movement of a diffusible suppression factor (or "silencing factor"), in order to enter and affect cells remote from the initial point of inoculation. The gene silencing may result in an altered phenotype; "altered phenotype" as used herein includes alterations in characteristics that can be visually observed (e.g., color), measured (e.g., average height or other growth characteristics) or biochemically assessed (e.g., presence of amounts of target gene products, including RNA, protein or peptide products, or downstream biochemical pathway products).

As used herein, an "endogenous" plant gene refers to a gene integrated into the chromosomal DNA of the plant genome. Endogenous genes include those that occur naturally in the plant genome, as well as those artificially introduced (such as by Agrobacterium-mediated transformation or ballistic bombardment).

As used herein, the term "silenced" or "gene silencing" refers to a reduction in the expression product of a target gene. Silencing may occur at the transcriptional or post-transcriptional level. Silencing may be assessed on the cellular level (i.e., by assessing the gene products in a particular cell), or at the plant tissue level (assessing silencing in a particular type of plant tissue) or at the level of the entire plant. Silencing may be complete, in that no final gene product is produced, or partial, in that a substantial reduction in the amount of gene product occurs. Such reduction may result in levels of gene product that are less than 90%, less than 75%, less than 50%, less than 30%, less than 20%, or even less than 10% that produced by non-silenced genes.

As used herein, "systemic silencing" refers to the silencing of genes in plants or plant tissues, where gene silencing occurs in cells that are remote from the site of initial inoculation of the DNA silencing episome. Applicants do not wish to be held to a single theory of systemic silencing; systemic silencing may occur by the replication and cell-to-cell movement of DNA constructs, or by the movement of an as-yet-unidentified mobile silencing factor. Systemic silencing does not require that every tissue or every cell of the plant be affected, as the effects and extent of silencing may vary from tissue to tissue, or among cells.

As used herein, the term "DNA silencing episome" or "DNA silencing vector" refers to a DNA construct capable of replicating within a host cell (either autonomously or as an integrated part of the host genome), and carrying a heterologous (or "recombinant") DNA sequence that is similar or identical in nucleotide sequence similarity to an endogenous host plant gene, or to a fragment of that plant gene. The heterologous DNA sequence is of sufficient sequence similarity to the endogenous gene that silencing of the endogenous gene occurs upon introduction of the episome. Such DNA sequences are substantially similar in nucleotide sequence to the endogenous sequence to be silenced; the heterologous DNA sequence may have from 60% sequence similarity, 70% sequence similarity, 75% sequence similarity, 80% sequence similarity, 85% sequence similarity, 90% sequence similarity, 95% sequence similarity, or even 97% or 98% sequence similarity, or more, to the target endogenous sequence.

As used herein, the term "heterologous DNA" contained on the DNA silencing episome refers to DNA that is not naturally found in conjunction with the DNA episomal construct, i.e., that has been introduced by genetic engineering techniques. The heterologous DNA may be identical in sequence to an endogenous target gene to be silenced, or may have extensive sequence similarity thereto. The heterologous DNA may be identical in sequence to, or share extensive sequence similarity to, a fragment of an endogenous target gene, where the fragment is of a size sufficient to silence the endogenous target gene. The heterologous DNA may be in sense or antisense orientation. One skilled in the art will be able, using techniques available in the art and without undue experimentation, to test and select gene fragments for their ability to induce silencing when used in the present methods.

A preferred embodiment of the present invention utilizes DNA episomes based on plant viral genomes. A particularly preferred embodiment utilizes episomes based on geminivirus genomes. Additional plant DNA viruses include that Cauliflower mosaic virus and the Badnaviruses. Heterologous DNA may replace the coding region for the viral coat protein (or any other open reading frame that is nonessential for the present purposes of gene silencing).

Novel recombinant geminivirus constructs including expression cassettes and transfer vectors are provided. The present geminivirus constructs, when transfected into a plant cell, act to silence a gene already present in the plant cell. The gene to be silenced may be an endogenous plant gene, or a gene or DNA sequence that has previously been artificially introduced into the plant cell. The present geminivirus constructs further provide a method for the systemic silencing of a gene in a plant, for example, by providing both the A and B genome components of the geminivirus to the subject plant.

Also provided are methods of making the expression vectors and methods of using them to produce transfected plant cells having an altered phenotype. The expression vectors include a heterologous nucleic acid sequence as defined above. A preferred embodiment is a geminivirus genome DNA wherein the coding sequence of the coat protein gene has been replaced (in whole or in part) with the heterologous DNA sequence. Where a bipartite geminivirus genome is utilized, the DNA A genome component may include as operably linked components a transcription initiation unit (such as the geminivirus coat protein gene (AR1) promoter), a heterologous nucleic acid sequence as defined above, and a transcription termination region. The altered DNA A component may be transfected into a plant cell simultaneously with the DNA B component of that geminivirus; alternatively, the DNA-A and DNA-B components may be combined in a binary plasmid.

A transfected plant cell may be produced by contacting the plant cell with the recombinant DNA episome, such as a recombinant geminivirus transfer vector described above. Where a geminivirus construct containing both the DNA-A and DNA-B bipartite genome components is used, the components can be introduced into a plant cell on separate plasmids or carried together on a single DNA construct.

Thus the DNA constructs of the present invention include various forms, depending on the intended use of the construct. Constructs include vectors, transcriptional cassettes, expression cassettes, and binary plasmids. Where systemic silencing is desired, the construct must be capable of both replication in the host cell, and cell-to-cell movement (either of the DNA construct or a silencing factor).

A preferred recombinant episomal silencing construct contains a heterologous nucleotide sequence, which may be any sequence having sequence identity to, or substantial sequence similarity to, an open reading frame of an endogenous gene encoding a polypeptide of interest (for example, an enzyme). Alternatively or in addition, the heterologous nucleotide sequence may be identical to or have substantial sequence similarity to an endogenous genomic sequence, where the genomic sequence may be an open reading frame, an intron, a noncoding leader sequence, or any other sequence which inhibits transcription, messenger RNA processing, for example, splicing, or translation.

The heterologous DNA segment carried by the silencing construct may represent only a fragment of the endogenous gene to be silenced; the present inventors have shown that fragments of genes, in either the sense or antisense orientation, are sufficient to induce silencing.

A preferred DNA silencing construct comprises a DNA origin of replication, preferably from a plant DNA virus such as a geminivirus. The construct further includes DNA encoding any proteins necessary for replication of the DNA construct. For example, the origin of replication and DNA encoding necessary replication proteins may be obtained from the same geminivirus species; alternatively, the origin of replication may be from one geminivirus species and the replication proteins from a different geminivirus species. The construct further includes a DNA segment identical to, or having substantial sequence similarity to, an endogenous plant DNA segment to be silenced.

Episomal silencing constructs that utilize portions of DNA plant virus genomes do not have to include the viral movement protein genes to accomplish gene silencing. The present inventors have determined that the viral movement proteins are non-essential for episomally-mediated gene silencing. Because movement of the viral genome is not believed to be required for systemic silencing, the host plant need not be one that is naturally susceptible to the virus on which the silencing construct is based. Particle bombardment techniques, as are known in the art, may be used to introduce a silencing construct into a cell, or group of cells, in a plant. Replication of the construct in the plant cell(s) leads to systemic silencing. While not wishing to be held to a single theory, applicants believe that systemic silencing is achieved by movement of either the construct DNA, or a mobile silencing factor, through the plant tissues.

The nucleotide sequences of this invention may be synthetic, naturally derived, or combinations thereof. Methods of producing recombinant DNA constructs are well known in the art.

Promoters

The present inventors have further determined that the DNA silencing episomes of the present invention need not have a promoter operably linked to the heterologous DNA segment therein. Use of a silencing construct carrying a heterologous DNA segment as described above, where that DNA segment is not operably linked to a promoter in the DNA construct, still results in silencing of the endogenous gene, and will result in systemic silencing. Use of a promoter operably linked to the heterologous DNA in the silencing construct may, however, increase the extent of the systemic silencing.

The present inventors have further determined that DNA constructs such as the geminivirus constructs described herein are capable of silencing endogenous plant promoters, where the DNA construct introduced into the target plant carries DNA having sequence identity to (or substantial sequence similarity to) an endogenous promoter sequence. Thus, where a family of homologous genes exist, but the associated promoters differ, selective silencing of one member of the gene family may be achieved by suppressing its promoter, using episomal constructs of the present invention. Such promoters may be tissue-specific (e.g., promoters associated with leaf-specific actins, as compared to actins expressed in other plant tissues) or developmentally regulated promoters. Examples of such promoters are known in the art.

Methods

The present methods are useful in suppressing the production of undesired gene products (e.g., sugars or other products contributing to the flavor, color or composition of a plant product). Systemic or tissue-specific suppression of a particular endogenous protein product may be desirable where the plant has been transformed to express a protein product of interest; suppression of endogenous proteins may lead to increased production of the transgene of interest.

Improved methods of isolating and sequencing gene sequences have provided many isolated plant DNA segments of unknown function. Methods of determining the function of DNA segments have not kept pace with methods of isolating or determining the sequence of DNA segments. The present constructs and methods provide a method of rapidly and reproducibly screening plant DNA fragments of unknown function to determine their function in plant tissue or intact plants, using episomally-mediated homology-dependent gene silencing. Such screening methods would include the preparation of a episomal silencing construct containing heterologous DNA identical to or having substantial sequence similarity to the target sequence; inoculating host plants with the silencing construct and, after a period of growth, comparing the inoculated host with an uninfected control plant. Constructs based on geminivirus and badnavirus genomes are particularly useful, as these viruses are known to infect a wide variety of agriculturally important crop plants. Characteristics for comparing test and control plants include growth characteristics, morphology, observable phenotype, and biochemical composition. The differences between the test and control plants indicate the function of the silenced DNA sequence. The period of growth necessary for any differences in the treated and control plants to become apparent will vary depending on the host plants used and the function of the DNA being suppressed, as will be apparent to one skilled in the art. Such periods may range from several days, a week, two weeks, three weeks or four weeks, up to six weeks, eight weeks, three months, six months or more. Because the present method does not require tissue culture or selection to obtain alterations in gene expression, the methods can be adapted to automation for large-scale screening of anonymous sequences for function in plants. As used herein, "screening" of a DNA segment does not imply that the function of the DNA segment will be positively identified in every case. As used herein, an "unidentified" plant gene or DNA segment is one whose functional role in the plant is unknown, even though the nucleotide sequence may be known.

The present invention also provides methods for rapidly and reproducibly screening portions of an isolated plant gene of known function, to identify those portions or fragments of genes that are effective in preventing or suppressing expression. Such screening methods will lead to refinements in current methods of gene suppression using sense and antisense DNA.

The present DNA episomal silencing system provides advantages over RNA viral vectors that are currently in use for testing gene function. Infection with RNA viruses requires that infectious transcripts be made in vitro, capped, and mechanically inoculated. Other "knock-out" systems in plants rely on chromosomal transformation, which can be time-consuming. Unlike RNA virus-derived vectors, foreign DNA is stably maintained in geminivirus vectors and cloned DNA isolated from *E. coli* can be used directly for inoculation of intact plants, e.g., by particle bombardment. Infectious DNAs can be easily generated from shuttle vector libraries containing large segments of cDNA sequence. The present inventors have shown that as little as 150 base pairs of transcribed sequence can result in effective silencing, obviating the need for cloning full-length cDNAs. Promoter sequences have also been silenced by TGMV vectors, indicating that individual members of gene families can be selectively silenced where their promoters differ sufficiently from one another. Geminivirus and badnavirus vectors can be developed for different families of plants, thus allowing genes to be characterized directly in a species of interest. The present invention can also be used to identify single gene traits in a variety of species. Libraries of genes can be tested by subjecting plants to a screen for a single gene trait, such as pathogen resistance, and then looking for susceptible plants whose gene for resistance has been silenced. Current mutagenesis techniques require screening of segregating progeny, which can be time-consuming and is not feasible for many species that carry genes of interest.

Subject Plants

Plants which may be employed in practicing the present invention include any plant (angiosperm or gymnosperm; monocot or dicot) in which DNA constructs according to the present invention can replicate and, where systemic silencing is desired, where movement of the DNA construct or a silencing factor occurs. Particularly preferred are those plants susceptible to infection by plant geminiviruses. As used herein, "susceptible to infection" includes plants that are naturally infected by geminiviruses in the wild, plants that can be mechanically inoculated with the DNA construct, or that can be inoculated by methods other than mechanical inoculation (such as by Agrobacterium inoculation). "Susceptible to infection" refers to plants in which the DNA construct is able to replicate within the inoculated plant cell.

Suitable plants for use in the present methods include (but are not limited to) legumes and solanaceous species. Specific plants suitable for use in the present invention included, but are not limited to, tobacco (*Nicotiana tabacum*), potato (*Solanum tuberosum*), soybean (glycine max), peanuts (*Arachis hypogaea*), cotton (*Gossypium hirsutum*), squash, sweet potato (*Ipomoea batatus*), cassava (*Manihot esculenta*), beets, sugar beets (*Beta vulgaris*), and tomato (*Lycopersicon esculentum*).

A variety of techniques are available in the art for introduction of DNA constructs into a plant cell host. These include Agrobacterium-mediated transfection, injection, electroporation, microparticle bombardment, etc. In a preferred embodiment, intact plants are inoculated using microprojectiles carrying a geminivirus construct according to the present invention, that includes both the A and B DNA components. The site of inoculation will be apparent to one skilled in the art; leaf tissue is one example of a suitable site of inoculation. Inclusion of the B component of the geminivirus genome results in systemic effects, gene silencing is seen at sites remote from the original point of inoculation.

The examples which follow are set forth to illustrate the present invention, and are not to be construed as limiting thereof.

EXAMPLE 1

Materials and Methods: Vector Construction

Figure 1B:
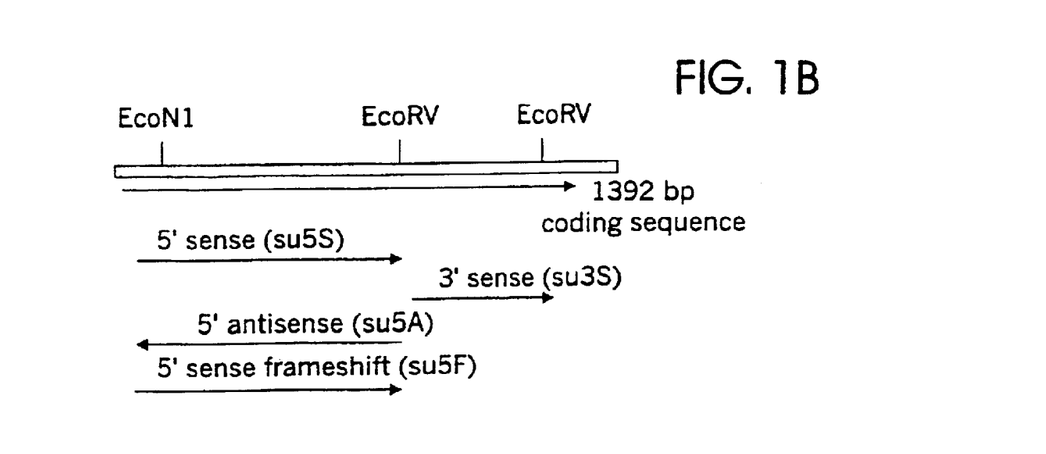
FIG. 1B depicts the magnesium chelatase gene (su) cDNA, which includes 23 bp of upstream, non-coding sequence and a 1392 bp coding sequence. A 786 bp 5' fragment in sense orientation (su5S) was used to make TGMV::su5S. TGMV::su5F has a frameshift in the su coding sequence. TGMV::su5A contains a 786 bp 5' fragment in inverse (antisense) orientation. A 403 bp 3' fragment in sense orientation was used to make TGMV::su3S.
Figure 1C:
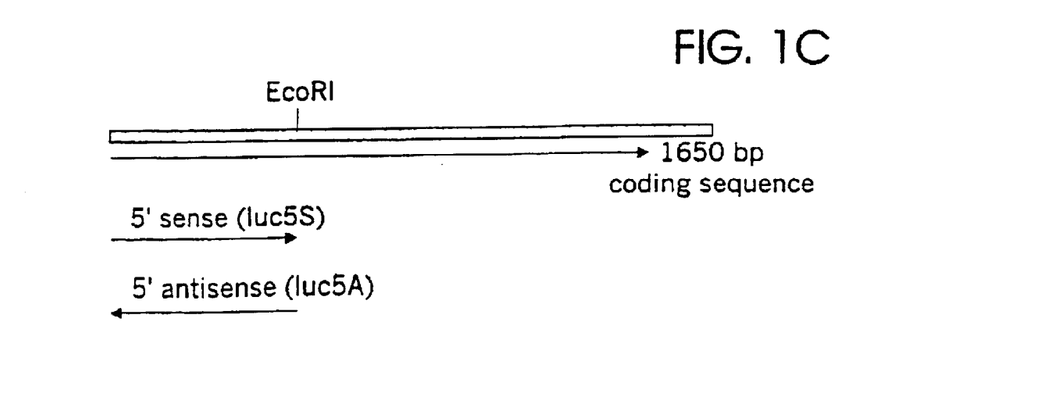
FIG. 1C depicts the firefly luciferase gene (luc), along with two fragments derived from this gene used to make TGMV::luc constructs. A 623 bp fragment extending from the 5' end of the gene to the EcoR1 site was cloned into TGMV in sense (luc5S) and anti-sense (luc5A) orientations.

FIG. 1A depicts the TGMV A and B genetic components; each contains a common region (CR) that includes the origin of replication. AL1, AL2, and AL3 are viral genes needed for replication and gene expression. The AR1 gene encodes the coat protein and was replaced with the heterologous DNA fragments shown in FIGS. 1B and 1C to produce the TGMV-derived episomes used herein. The B component encodes two movement proteins, BL1 and BR1.

TGMV-A-derived vectors were constructed using the pMON1655 plasmid, a pUC-based plasmid with 1.5 tandem copies of TGMV-A containing the AR1 coding sequence replaced by a short polylinker, and retaining the AR1 promoter and terminator sequences. pl-VN44 is a full length 1392 bp cDNA of the nucleotide-binding subunit of magnesium chelatase isolated from *Nicotiana tabacum* cv. SR1 (Nguyen, *Transposon tagging and isolation of the sulfur gene in tobacco*, Ph.D. Thesis, North Carolina State University (1995)). Magnesium chelatase is a multi-subunit protein that catalyzes the insertion of magnesium into protoporphyrin IX (Jensen et al., *Molec. Gene Genetics* 250:283 (1996)). In tobacco, a mutated allele (Su) of one subunit causes the phenotype known as 'sulfur'. *Nicotiana tabacum* plants homozygous for this allele are yellow (Su/Su), and heterozygous plants are yellow-green (Su/su).

A 786 bp Acc661/EcoRV fragment from the 5' end of the su cDNA (including the start codon and 17 bp of 5' non-coding sequence) was cloned into pMON1655 in both orientations, resulting in two TGMV constructs: the 5' su fragment driven by the TGMV AR1 promoter in the sense orientation (TGMV::su5S) and the anti-sense orientation (TGMV::su5A).

The sense reading frame of the su gene was disrupted by cleaving and filling an EcoNI restriction enzyme site to create a stop codon 104 bp from the initiator ATG to produce TGMV::su5F.

TGMV::su3S contains a 403 bp EcoRV fragment in sense orientation that ends 108 bp upstream of the putative stop codon.

The plasmids TGMV::luc5S and TGMV::luc5A contain a 623 bp EcoR1/BglII fragment of the 5' end of the full-length (1660bp) firefly luciferase gene (Ow et al., *Science* 234:866 (1996)) cloned into pMON1655 in the sense and anti-sense orientations, respectively. This fragment of the firefly luciferase gene contains 26 bp of 5' non-coding sequence and retains the luciferase start codon.

A plasmid containing 1.4 tandem copies of the TGMV B component (pTG1.4B, Fontes et al., *Plant Cell* 8:405 (1994)) was used with the TGMV-A constructs for all inoculations described herein, unless otherwise noted.

Table 1 describes the TGMV-A constructs used for the experiments described herein.

TABLE 1

TGMV-A constructs

| Name | Heterologous insert |
|---|---|
| TGMV::su5S | 786 bp fragment of 5' end of su gene, sense orientation |
| TGMV::su3S | 403 bp fragment of 3' end of su gene, sense orientation |
| TGMV::su5A | 786 bp fragment of 5' end of su gene, antisense orientation |
| TGMV::su5F | frameshifted su gene, sense orientation |
| TGMV::luc5S | 623 bp fragment of 5' end of firefly luciferase gene, sense orientation |
| TGMV::luc5A | 623 bp fragment of 5' end of firefly luciferase gene, antisense orientation |

EXAMPLE 2

Materials and Methods: Plant Infections, DNA and RNA Analysis

Three-week-old *N. benthamiana* plants were used for bombardment. The BIOLISTIC® Particle Delivery System (Bio-Rad, Hercules, Calif., USA) was used to infect *N. benthamiana* plants as described previously (Nagar et al., *Plant Cell* 7:705 (1995)). Total DNA from infected and healthy plants was isolated (Dellaporta et al., *Plant Molec. Biol. Rep.* 1:19 (1983)), blotted and probed with labeled DNA corresponding to the TGMV-A AL1, AL2, AL3 reading frames, or 786 bp of su. Total RNA was isolated from infected or mock-infected leaf and stem tissue as described (Kaufman et al., *Plant Physiol.* 78:388 (1985)). Glyoxylated RNA was fractionated, blotted and hybridized with RNA probes as described (Frances et al., *Plant Cell* 4:1619 (1992)).

Transgenic plants were imaged using a photon-counting imaging system (Hamamatau Photonic Systems, Bridgewater, N.J., USA) as described (Millar et al, *Plant Cell* 4:1075 (1992)). Systemically infected or control leaves were excised and immediately submerged in a 0.01 mg ml$^{-1}$ p-luciferin solution for precisely 5 minutes before being placed in the imaging chamber.

EXAMPLE 3

Plants Infected with TGMV::su display a Variegated Phenotype

To determine if TGMV could be used as a vector to silence plant gene expression, we tested fragments of su inserted into TGMV-A in place of the AR1 coding sequence, transcribed from the AR1 promoter (Example 1 and Table 1, above). Sequences from su were used because down-regulation of the endogenous gene was likely to produce a visible phenotype (lack of chlorophyll). Although the cDNA used was from *N. tabacum*, the sulfur alleles of *N. tabacum* and *N. benthamiana* showed 95% nucleotide sequence conservation over the 5' and 3' fragments used in this study (unpublished observations).

*N. benthamiana* plants were infected using particle gun bombardment to deliver cloned viral DNA. Wild-type TGMV produced chlorotic, irregular spots on inoculated leaves approximately 5 days after bombardment; leaf curling and chlorosis were apparent at 5–7 days. In contrast, leaves inoculated with TGMV::su5S showed discrete, round, yellow spots after 3–5. days (data not shown). Not all yellow spots produced by TGM::su5S were circular, but most had a distinct border between green and yellow tissue that was absent in plants infected with wildtype TGMV and in TGMV vectors carrying luc fragments. 'Spots' produced by inoculation of TGMV::luc and wt TGMV occurred later, were infrequent, and had mixtures of green and yellow cells (data not shown). Individual spots produced by TGMV::su5S varied in size from 1 to 3 mm and had an area of cells lacking chlorophyll that corresponded to at least 500–800 epidermal cells.

Variegation was produced by systemic infection with the TGMVA::su constructs. As new leaves emerged subsequent to inoculation, large yellow-white or green sectors developed, often emanating from vascular tissue (data not shown). The patterns of variegation differed from plant to plant and from leaf to leaf.

In many plants, yellow or white tissue was confined to areas adjacent to the veins. In other plants, large sectors of mesophyll tissue were affected. White tissue likely resulted from bleaching of carotenoids. Microscopic examination of fixed tissue showed no evidence of necrosis or cell death in areas lacking chlorophyll. A cross-section of leaves from TGMV::su5S infected plants and control plants showed that TGMV::su5S-infected leaf had a uniform lack of chlorophyll, compared to a mock-inoculated control leaf. When both leaves were viewed with fluorescence to detect DAPI-stained DNA, both leaves indicated the presence of intact nuclei.

Replacement of the AR1 gene by foreign DNA, such as su is known to attenuate symptoms (Gardiner et al., *EMBO J.* 7:899 (1988)). Wild-type TGMV also produced chlorotic lesions, but these lesions usually contained collapsed cells. A striking feature of the variegated plants was the stem tissue, which was either striped yellow and green, uniformly yellow, or white (data not shown). Neither chlorotic lesions or any other visible symptoms (other than stunting) were seen on stems of wild-type TGMV-infected plants, although stem tissue of such plants occasionally contains collapsed cells (Nagar et al., Plant Cell 7:705 (1995)).

Systemic variegation required TGMV-B in addition to a TGMV-A construct. TGMV-B contains two genes required for viral movement. When TGMV::su5S was bombarded in the absence of the TGMV-B component, yellow spots were produced but systemic variegation was not detected (data not shown). Wild-type TGMV-A inoculated without TGMV-B did not show visible spots, probably because the TGMV-B component is required for symptom formation (von Arnim and Stanley, *Virology* 196:288 (1992)).

EXAMPLE 4

Variegation is Not Caused by Mutant Proteins

The mutant Su allele cloned from *N. tabacum* has a single mis-sense mutation causing an altered amino acid (Nguyen, *Transposon tagging and isolation of the sulfur gene in tobacco*, Ph.D. Thesis, North Carolina State University (1995)). This polypeptide has been hypothesized to stably interfere with the function of the heteromeric magnesium chelatase complex, causing a light green phenotype in heterozygous plants. Translation of RNA from the wild type 785 bp su fragment included in TGMV:su5S may produce a truncated polypeptide that would similarly disrupt assembly of the heteromeric complex. To test this hypothesis, we introduced a frameshift mutation into the su fragment 104 bp downstream of the start codon to produce TGMV::su5F. The wild-type su polypeptide is 424 amino acids, including the putative transit sequence. The frameshift mutation was predicted to yield a truncated polypeptide with only 35 amino acids homologous to the su protein. If translation were to re-initiate at the next AUG (position 99), it would produce a polypeptide lacking a transit sequence that would be unlikely to be imported into the chloroplast. There were no repeatable differences in the variegation produced in plants inoculated with TGMV::su5S or TGMV::su5F (data not shown) suggesting that defective protein interactions in the chloroplast were not responsible for the yellow phenotype.

Plants bombarded with TGMV::su5A or TGMV::su3S also produced variegation similar to that seen with TGMV::su5S. The 5' anti-sense and the 3' sense fragments lack sequences for functional transit peptides, yet each was as effective as the 5' sense fragment of su in producing yellow spots and systemic variegation. These results indicate that down-regulation of su gene function is more likely to result from interactions at either the RNA or DNA level, than from defective protein-protein interactions.

The original su cDNA was tested in a plasmid vector incapable of replicating in plant cells (pLVN44) to determine if TGMV was required for homology dependent silencing of su. No systemic variegation occurred and no yellow spots on the bombarded leaves were observed.

To determine if tissue recovered from TGMV::su-infected tissue retained the variegated phenotype, plants were regenerated from sectors of systemically infected *N. Benthamiana*. Explants were taken from yellow/white (no chlorophyll), variegated, or green tissue of plants infected with TGMV::su5S. Variegated plants were recovered from yellow/white or variegated tissue (results not shown). In addition, one plant regenerated from yellow/white tissue was fully green, with no indication of variegation. Unlike the variegated regenerants, the green plant lacked viral DNA, as determined by DNA gel blot hybridization analysis (data not shown).

To determine if the TGMV::su constructs had integrated into chromosomal DNA, regenerated plants that retained variegation were allowed to set seed. Seed harvested from flowers with white stems and sepals (which are normally green) produced green, wild-type seedlings, as did all seed harvested from variegated plants. This result indicates that the TGMV::su sequences did not integrate into chromosomal DNA at significant frequencies and/or that any chromosomal form of TGMV::su was not sufficient to cause silencing of the endogenous su alleles.

EXAMPLE 5

Endogenous Su mRNA Levels are Reduced in Yellow Sectors of TGMV/su-Infected Plants Some phloem-limited geminivirus cause yellow mosaic leaf tissue. We considered the possibility that TGMV::su-induced variegation reflected altered symptomology of the engineered virus rather than a reduction of su mRNA.

Figure 2:
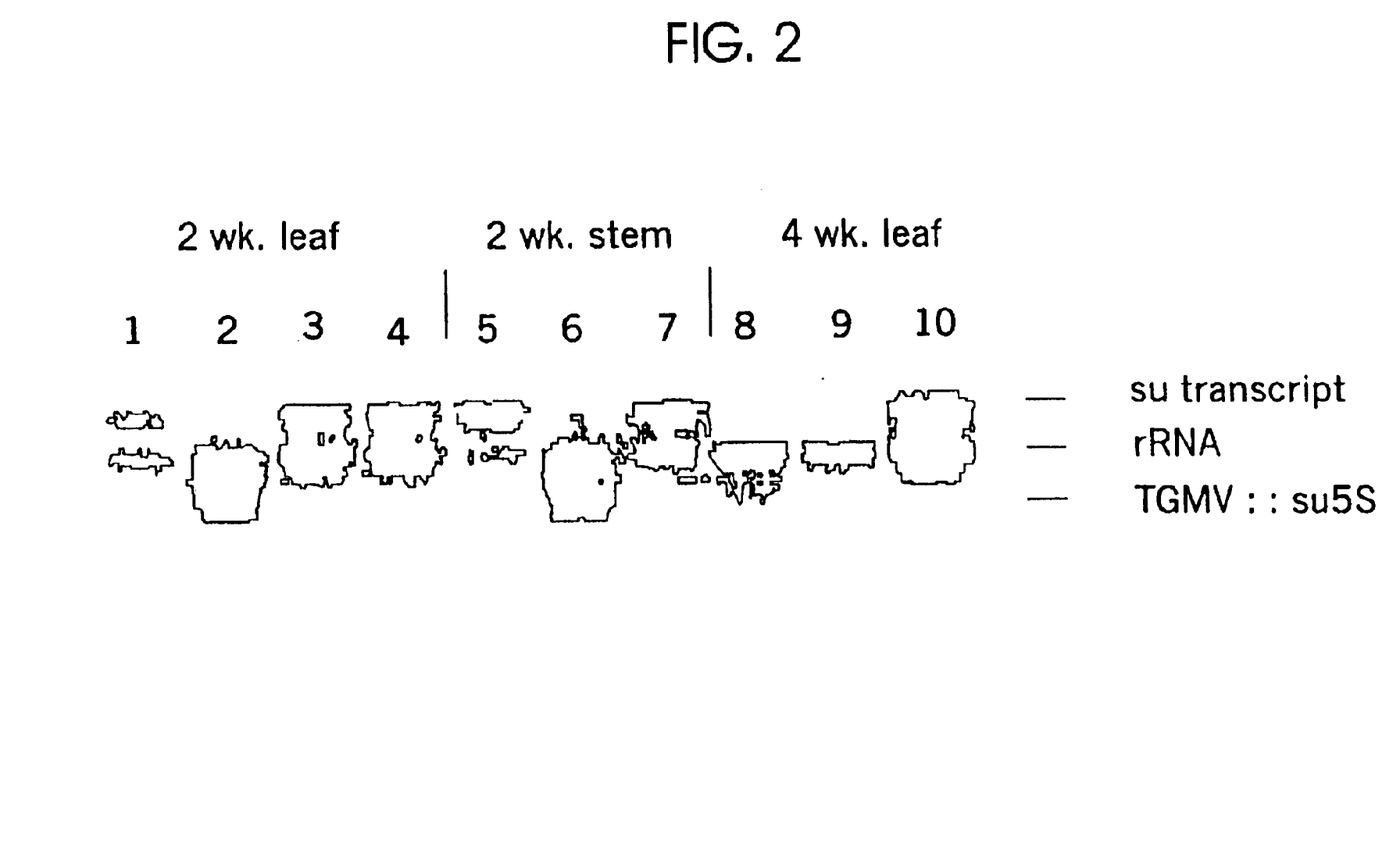
FIG. 2 shows the results of probing total RNA isolated from leaf and stem tissues to detect the accumulation of endogenous su mRNA. Lanes labeled "2 wk leaf" and "2 wk stem" show RNA harvested from plants 14 days post infection. "4 week" leaf tissue consists of leaves at a similar developmental stage as 2 week tissue (young, expanded), but taken from older plants (28 days post infection). Lanes 1, 5 and 10 contain RNA from uninfected control tissue; lanes 2, 6, and 9, TGMV::su5S-infected tissue; lanes 3 and 7, TGMV::luc5S-infected tissue; lane 4, wild-type TGMV-infected tissue; and lane 8, TGMV::su5F-infected tissue. TGMV::su-infected plants showed reduced accumulation of endogenous su MRNA. The episomal transcript is labeled TGMV::su5S and corresponds to the su transcript from the AR1 promoter of TGMV::su.

TGMV::su-infected plants showed reduced accumulation of endogenous su mRNA. Total RNA was isolated from particle bombarded leaf and stem tissue (control) and leaf and stem tissue from plants systemically infected with TGMV::su5S, TGMV::su5F; TGMV::luc, or wildtype (wt) TGMV. Leaf material from TGMV::su-infected plants contained some green tissue but the majority was yellow or white, while stem tissue was uniformly green (control, wild-type) or white (TGMV::su5S and TGMV::su5F). As shown in FIG. 2, 15 µg of total RNA isolated from leaf or stem tissue was loaded in each lane. The blot was probed with a $^{32}$P-labeled RNA transcript made from pLVN44 containing the su cDNA clone. The 18s rRNA band served as a loading control. The episomal transcript is labeled TGMV::su5S and corresponds to the su transcript from the AR1 promoter of TGMV::su. Lanes labeled "2 wk leaf" and "2 wk stem" show RNA harvested from plants 14 days post infection. "4 week" leaf tissue consists of leaves at a similar developmental stage as 2 week tissue (young, expanded), but was taken from older plants (28 days post infection). Lanes 1, 5 and 10 show RNA from uninfected control tissue; lanes 2, 6, and 9, TGMV::su5S-infected tissue; lanes 3 and 7, TGMV::luc5S-infected tissue; lane 4, wt TGMV-infected tissue; and lane 8, TGMV::su5F-infected tissue.

FIG. 2 shows that a transcript of the endogenous su gene at the expected size was present in control and wt TGMV-infected stem tissue (lanes 1, 4, 5 and 10) but lacking in TGMV::su5S-infected leaf and stem tissue (lanes 2, 6 and 9). RNA from tissue infected with TGMV::su5S also contained a transcript corresponding to the viral 786 bp su fragment. Accumulation of this transcript was attenuated in leaf tissue at a later stage of viral infection (compare lanes 2 and 6 containing tissue two weeks' post-infection, to lane 9 containing tissue at 4 weeks' post-infection). Lane 8 shows that tissue infected with TGMV carrying the 786 bp fragment with a frameshift mutation also lacked the full length su transcript from the endogenous gene.

The level of endogenous su transcription was also tested in plants infected with TGMV::luc5S. TGMV::luc has no homology to plant DNA; it shows stable movement but attenuated symptoms. The level of su transcript in TGMV::luc-infected leaf material (FIG. 2, lanes 3 and 7)was similar to that of the control (FIG. 2, lanes 1, 5 and 10).

EXAMPLE 6
Downregulation of Transgene expression

We used transgenic luciferase plants to determine if episomal TGMV sequences could silence expression of a foreign gene. *N. benthamiana* plants stably transformed with luc driven by the 35S CaMV promoter were bombarded with TGMV::luc5S and TGMV::luc5A, containing a 623 bp 5' transcribed luc sequence in sense or anti-sense orientation. Leaves were imaged 14 days post inoculation and compared to leaves from *N. benthamiana* controls (inoculated with particles only) or those inoculated with wild-type TGMV. Photon density from low to high was displayed in photographic images as blue, green, yellow, red and white (not shown).

Areas with both high and low luciferase activity were found in leaves from uninfected control plants and in plants systemically infected with wt TGMV 2 weeks after inoculation (results not shown). Only low levels of luciferase activity were found in leaves infected with TGMV::luc5S and TGMV::luc5 A. The complete absence of high level luciferase activity was surprising as viral infections are non-uniform. These results indicate that luciferase transgene expression is downregulated by TGMV::luc.

Figure 3:
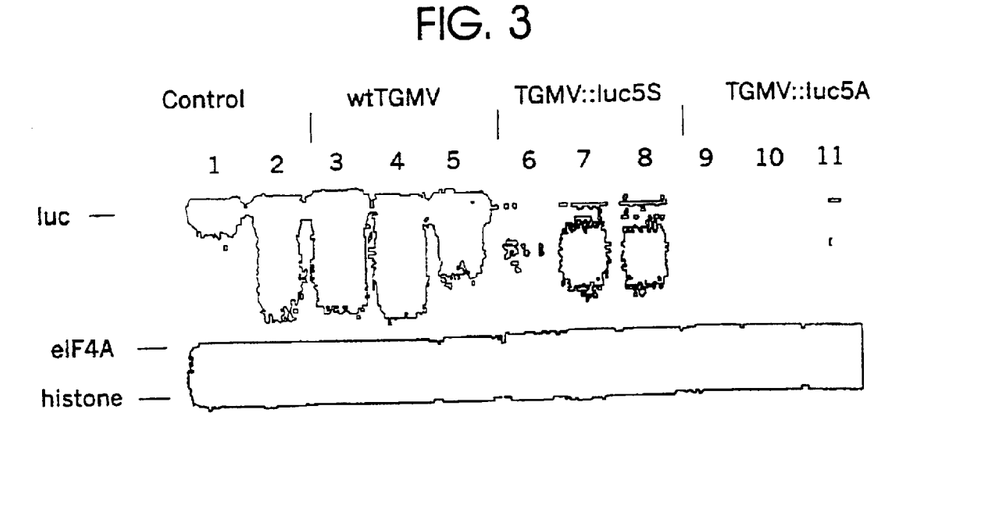
FIG. 3 shows the results of probing RNA harvested from plants 21 days post inoculation, with a luc RNA probe (luc), a probe for the constitutively expressed eIF4A gene (eIF4A), and a probe for the constitutively expressed histone H1 gene (histone). Tissue was taken from two sham-inoculated plants (lanes 1–2), three plants infected with wildtype TGMV (lanes 3–5); three plants infected with TGMV::luc5S (lanes 6–8); and three plants infected with TGMV::luc5A (lanes 9–11). The luciferase transcript is downregulated by TGMV::luc. Degradation of the luc message in some of the samples is indicated by the smear below the full length luc transcript.

RNA from uninfected control and infected plants was analyzed to determine if the reduced luciferase activity was caused by a reduction in mRNA accumulation. FIG. 3 shows total RNA isolated from the same plants as described immediately above, 3 weeks after infection. RNA was isolated from the top three inches of each of the plants and included systemically infected leaves, stems and meristematic areas, but not inoculated leaves; 5 µg of total RNA loaded in each lane. Blotted RNA was probed with a $^{32}$P-labeled luc RNA probe (see top panel of FIG. 3) or probes for the constitutively expressed genes eIF4 A (bottom panel, FIG. 3) and histone H1 (bottom panel, FIG. 3).

FIG. 3 shows RNA from two particle bombarded plants (controls; lanes 1–2); three plants each infected with wild-type (wt) TGMV (lanes 3–5); three plants each infected with TGMV::luc5S (lanes 6–8); and three plants each infected with TGMV::luc5A (lanes 9–11). Degradation of the luc message in some of the samples is seen in the smear below the full length transcript.

The amount of luc transcript was greatly reduced in plants bombarded with TGMV::luc compared to both control and wt TGMV-infected plants. Accumulation of the luc transcript in two of the wt TGMV-infected plants was higher than that of uninfected controls. Increased luciferase activity, detected by photon imaging, has also been noted in TGMV-infected plants 3–4 weeks after inoculation (unpublished observation), suggesting an enhancement of 35S CaMV promoter activity by TGMV.

To determine whether the reduction in luc transcript reflected a general reduction in cytoplasmic transcript accumulation, we examined the levels of mRNAs encoding elongation initiation factor 4A (eIF4A) and histone H1. The eIF4A gene is constitutively transcribed in meristematic, leaf, stem and root tissues of tobacco (Mandel et al., *Plant Mol. biol.* 29:995 (1996)). An RNA gel blot was hybridized with probes for eIF4A from tobacco and histone H1 from pea (Gantt and Key, *Eur. J. Biochem.* 166:119 (1987)) (FIG. 3). The level of both the eIF4A and histone H1 transcripts were similar for wt TGMV-infected and TGMV::luc-infected plant tissue. These results demonstrate that the TGMV::luc constructs cause a specific reduction in luc mRNA accumulation.

EXAMPLE 7
Tissue with Incomplete Silencing Contains Higher Viral DNA Levels

Figure 4:
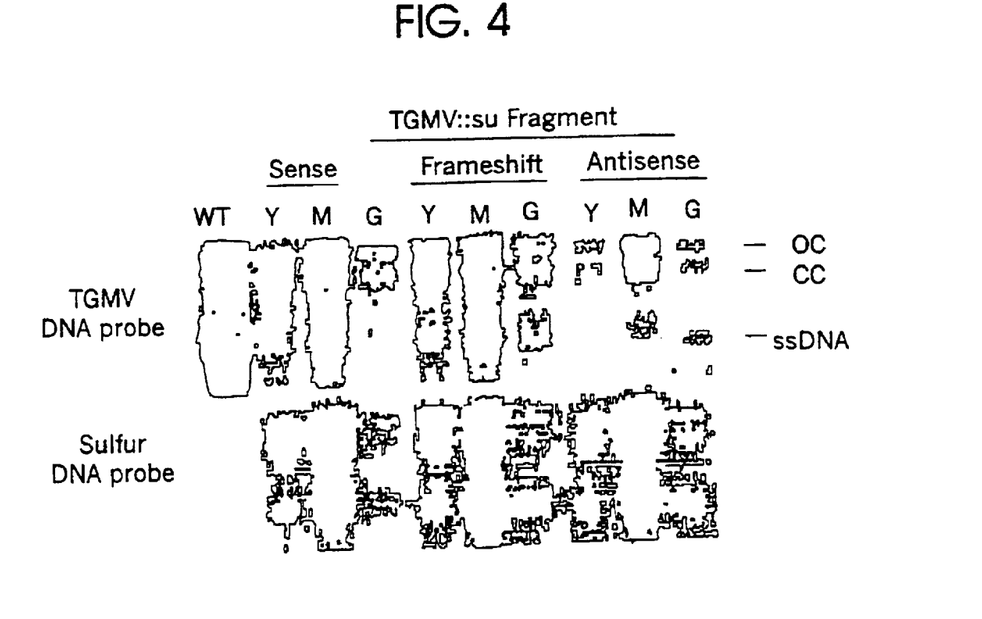

To determine whether a direct relationship existed between the presence of viral DNA and silencing, gel blot hybridization analysis of DNA isolated from leaves systemically infected with TGMV::su5S, TGMV::su5A or TGMV::su5F (FIG. 4) was performed. Variegated leaf tissue was separated into three categories: green tissue (G), yellow tissue (Y) and mixed (M). Green tissue had no apparent silencing phenotype or viral symptoms. The yellow category included yellow and white tissue that lacked chlorophyll, while mixed tissue contained light green regions and borders between yellow and green tissue. Uncut DNA was electrophoresed, blotted to membranes and probed with an 850 bp TGMV-A-specific DNA fragment and results are shown in FIG. 4. Lane 1 shows wildtype (wt) TGMV DNA with three DNA forms: open circular (OC), closed circular (CC) and ssDNA. Lanes 24 show DNA isolated from plants infected with TGMV::su5S. Lanes 5–7 show viral DNA from *N. benthamiana* inoculated with TGMV::su5F and lanes 8–10, TGMV::su5 A. The bottom panel of FIG. 4 shows the same blot as above but probed with a 786 bp fragment from su.

Green, healthy tissue showed a low amount of viral DNA (FIG. 4) indicating that some cells in the green tissue were infected. Viral DNA levels were higher in mixed tissues than they were in yellow tissue. The stability of the viral su insert was shown by a lack of smaller fragments corresponding to deleted forms of TGMV::su. Each of the TGMV::su constructs tested showed the same pattern, with the highest viral DNA levels in mixed tissues. This experiment was repeated several times with variable results. However, none of the plants ever had higher viral DNA levels in yellow tissue than in mixed tissue.

The ratio of ss DNA to ds DNA in plants infected with the TGMV::su constructs (which lack the AR1 coat protein gene) is lower than it is in wild-type TGMV infections (FIG. 4). The AR1 protein encapsidates ssDNA, forming inclusion bodies in plant nuclei (Rushing et al., *Phytopathology* 77:1231 (1987)), and the absence of the ARI protein is known to reduce ssDNA accumulation (Poome et al., *Virology* 218:264 (1996); Sunter and Bisaro, *Plant Cell* 4:1321 (1992)).

In principle, viral DNA in the yellow tissue might have been degraded as a result of a host response to viral infection. However, microscopic examination of DAPI-stained vibratome sections from yellow-white sectors showed intact, healthy cells (results not shown) and viral DNA isolated from such tissue did not appear more degraded than DNA isolated from 'mixed' or green tissue (FIG. 4). Furthermore, ethidium bromide-stained gels of uncut total DNA from yellow tissue showed no signs of chromosomal DNA degradation (data not shown). To exclude wild-type contamination, the same blots were striped and reprobed with the 786 bp su fragment. This probe hybridized to both ssDNA and dsDNA from each of the TGMV::su constructs (FIG. 4). These experiments suggest that su gene silencing is not simply proportional to viral DNA accumulation.

EXAMPLE 8

Silencing Vector Based on TGMV

A vector was developed from the A component of the bipartite TGMV genome, and used to facilitate the "knock-out" screening of plant DNA sequences. The vector has two origins of replication, one that functions in *Escherichia coli* and one that functions in the host, or target, plant (the plant in which it is desired to silence a gene). The vector also contains a multiple cloning site for insertion of heterologous plant DNA. Heterologous plant DNA refers to a DNA sequence that is not native to the geminivirus genome, but that is contained within a target plant; the DNA sequence may represent an endogenous plant gene, or a transgene that has been introduced into the target plant. The heterologous DNA had sequence identity to an endogenous target plant gene.

When the TGMV-A vector was bombarded into plants in conjunction with the TGMV-B component, silencing of the target plant genes was seen systemically in the plant (i.e., at sites remote from the site of bombardment). It is not yet clear whether the vector was moving through the plant, or whether a diffusible component distinct from the vector was causing systemic silencing. Although the TGMV episome is believed to replicate in only a few plant cells, silencing of the target endogenous plant gene was extensive and occurred throughout vegetative and floral parts of the plant. Viral disease symptoms were greatly attenuated in plants infected with the present construct (compared to infection with a wild-type geminivirus).

The foregoing examples are illustrative of the present invention, and are not to be construed as limiting thereof. The invention is described by the following claims, with equivalents of the claims to be included therein.

That which is claimed is:

1. A geminivirus silencing vector comprising a geminivirus genome comprising the geminivirus AL1, AL2 and AL3 coding sequences and heterologous DNA, said heterologous DNA comprising, in sense orientation, a fragment of a gene endogenous to a plant, wherein silencing of the endogenous gene is induced when the vector replicates in, and the fragment is transcribed in, a plant that comprises said endogenous gene.

2. The vector according to claim 1, wherein said heterologous DNA replaces a segment of the coding sequence for the geminivirus coat protein.

3. The vector according to claim 1, wherein said heterologous DNA is operably linked with the geminivirus coat protein promoter.

4. A DNA construct comprising a geminivirus genome wherein the DNA encoding the geminivirus coat protein has been replaced in part or in total with heterologous DNA comprising, in sense orientation, a fragment of an endogenous plant gene, and wherein silencing of the endogenous gene is induced when the geminivirus genome replicates in, and the fragment is transcribed in, a plant that comprises said endogenous gene.

5. The DNA construct according to claim 4, wherein said heterologous DNA is operably linked with a promoter.

6. The DNA construct according to claim 5, wherein said promoter is the geminivirus coat protein promoter.

7. A plant cell comprising the geminivirus silencing vector according to claim 1.

8. A plant comprising a plurality of cells according to claim 7.

9. A geminivirus silencing vector comprising a Tomato Golden Mosaic Virus (TGMV) genome comprising heterologous DNA, said heterologous DNA comprising, in sense orientation, a fragment of a gene endogenous to a plant, wherein silencing of the endogenous gene is induced when the vector replicates in, and the fragment is transcribed in, a plant that comprises said endogenous gene.

10. The vector according to claim 9, wherein said gene endogenous to a plant occurs naturally in the plant genome.

11. A geminivirus silencing vector comprising an African Cassava Mosaic Virus (ACMV) genome comprising heterologous DNA, said heterologous DNA comprising, in sense orientation, a fragment of a gene endogenous to a plant, wherein silencing of the endogenous gene is induced when the vector replicates in, and the fragment is transcribed in, a plant that comprises said endogenous gene.

12. The vector according to claim 11, wherein said gene endogenous to a plant occurs naturally in the plant genome.

13. A DNA construct comprising a Tomato Golden Mosaic Virus (TGMV) genome, wherein the DNA encoding the TGMV coat protein has been replaced in part or in total with heterologous DNA comprising, in sense orientation, a fragment of an endogenous plant gene, wherein silencing of the endogenous gene is induced when the vector replicates in, and the fragment is transcribed in, a plant that comprises said endogenous gene.

14. The vector according to claim 13, wherein said gene endogenous to a plant occurs naturally in the plant genome.

15. A DNA construct comprising an African Cassava Mosaic Virus (ACMV) genome, wherein the DNA encoding the TGMV coat protein has been replaced in part or in total with heterologous DNA comprising, in sense orientation, a fragment of an endogenous plant gene, wherein silencing of the endogenous gene is induced when the vector replicates in, and the fragment is transcribed in, a plant that comprises said endogenous gene.

16. The vector according to claim 15, wherein said gene endogenous to a plant occurs naturally in the plant genome.

17. A method of silencing the expression of an endogenous plant gene in a plant cell, comprising inoculating said plant cell with a geminivirus silencing vector comprising a geminivirus genome which contains heterologous DNA, said heterologous DNA comprising a fragment of a gene endogenous to said plant cell, wherein episomal replication of said vector and transcription of said fragment in the plant cell results in silencing of said endogenous gene.

18. The method according to claim 17, wherein said endogenous gene occurs naturally in the genome of said plant cell.

19. A method of silencing the expression of an endogenous plant gene in a plant cell, comprising inoculating said plant cell with a DNA construct comprising a geminivirus genome, wherein the DNA encoding the geminivirus coat protein has been replaced in part or in total with heterologous DNA comprising a fragment of a plant gene endogenous to said plant cell, wherein episomal replication of said geminivirus genome and transcription of said fragment in the plant cell results in silencing of said endogenous gene.

20. The method according to claim 19, wherein said endogenous gene occurs naturally in the genome of said plant cell.

21. A method of systemically silencing expression of an endogenous plant gene in a plant, comprising inoculating said plant with a geminivirus silencing vector comprising a geminivirus genome which contains heterologous DNA, said heterologous DNA comprising a fragment of a gene endogenous to said plant, wherein episomal replication of said vector and transcription of said fragment in the plant results in silencing of said endogenous gene.

22. The method according to claim 21, wherein said endogenous gene occurs naturally in the genome of said plant.

23. A method of systemically silencing expression of an endogenous plant gene in a plant, comprising inoculating said plant with a DNA construct comprising a geminivirus genome, wherein the DNA encoding the geminivirus coat protein has been replaced in part or total with heterologous DNA comprising a fragment of an endogenous plant gene, wherein episomal replication of said genome and transcription of said fragment in the plant results in silencing of said endogenous gene.

24. The method according to claim 23, wherein said endogenous gene occurs naturally in the genome of said plant.

25. A geminivirus silencing vector comprising a Tomato Golden Mosaic Virus (TGMV) genome comprising the TGMV AL1, AL2 and AL3 coding sequences operably associated with an AL1 promoter, and heterologous DNA, said heterologous DNA operably associated with a TGMV coat protein promoter and comprising, in sense orientation, a fragment of a gene endogenous to a plant, wherein episomal replication of said vector and transcription of said fragment in the plant results in silencing of said endogenous gene.

26. A method of silencing the expression of an endogenous plant gene in a plant cell, comprising inoculating said plant cell with a geminivirus silencing vector according to claim 9.

27. A method of silencing the expression of an endogenous plant gene in a plant cell of a plant, comprising:

introducing a nucleic acid encoding the geminivirus movement proteins into said plant cell; and inoculating said plant cell with a geminivirus silencing vector comprising a geminivirus genome comprising heterologous DNA comprising a fragment of a gene endogenous to a plant, wherein episomal replication of said vector and transcription of said fragment in the plant results in silencing of said endogenous gene.

28. The method of claim 27, wherein said plant cell is a cell from a species of Nicotiana and said geminivirus silencing vector is a Tomato Golden Mosaic Virus (TGMV) silencing vector.

* * * * *